(12) United States Patent
Nicolson et al.

(10) Patent No.: US 8,524,254 B2
(45) Date of Patent: Sep. 3, 2013

(54) BIORESORBABLE POLYMERS

(75) Inventors: Donald Magnus Nicolson, Gargunnock (GB); Janet Anne Halliday, West Lothian (GB); Jukka Tuominen, East Kilbride (GB); Amaia Zurutuza, East Kilbride (GB)

(73) Assignee: Ferring B.V., Hoofddorp (NL)

(*) Notice: Subject to any disclaimer, the term of this patent is extended or adjusted under 35 U.S.C. 154(b) by 492 days.

(21) Appl. No.: 12/446,235

(22) PCT Filed: Oct. 15, 2007

(86) PCT No.: PCT/GB2007/003936
§ 371 (c)(1),
(2), (4) Date: Mar. 23, 2010

(87) PCT Pub. No.: WO2008/047100
PCT Pub. Date: Apr. 24, 2008

(65) Prior Publication Data
US 2010/0317745 A1    Dec. 16, 2010

(30) Foreign Application Priority Data
Oct. 18, 2006  (GB) .................................. 0620685.8

(51) Int. Cl.
*A61K 9/00* (2006.01)
(52) U.S. Cl.
USPC ....................................................... 424/400
(58) Field of Classification Search
None
See application file for complete search history.

(56) References Cited

U.S. PATENT DOCUMENTS

| | | | |
|---|---|---|---|
| 3,487,068 A | 12/1969 | Morozowich et al. |
| 3,565,991 A | 2/1971 | Short |
| 3,598,122 A | 8/1971 | Zaffaroni |
| 3,598,123 A | 8/1971 | Zaffaroni |
| 3,639,157 A | 2/1972 | Wunder et al. |
| 3,731,683 A | 5/1973 | Zaffaroni |
| 3,734,097 A | 5/1973 | Zaffaroni |
| 3,737,521 A | 6/1973 | Born |
| 3,760,805 A | 9/1973 | Higuchi |
| 3,797,494 A | 3/1974 | Zaffaroni |
| 3,830,907 A | 8/1974 | Short |
| 3,845,761 A | 11/1974 | Zaffaroni |
| 3,845,770 A | 11/1974 | Theeuwes et al. |
| 3,854,480 A | 12/1974 | Zaffaroni |
| 3,860,701 A | 1/1975 | Short |
| 3,867,933 A | 2/1975 | Kitrilakis |
| 3,881,043 A | 4/1975 | Rieser et al. |
| 3,892,842 A | 7/1975 | Zaffaroni |
| 3,896,819 A | 7/1975 | Zaffaroni |
| 3,901,852 A | 8/1975 | Shah |
| 3,916,898 A | 11/1975 | Robinson |
| 3,916,899 A | 11/1975 | Theeuwes et al. |
| 3,921,636 A | 11/1975 | Zaffaroni |
| 3,931,113 A | 1/1976 | Seeger et al. |
| 3,934,580 A | 1/1976 | Cournut |
| 3,941,880 A | 3/1976 | Short |
| 3,948,254 A | 4/1976 | Zaffaroni |
| 3,948,262 A | 4/1976 | Zaffaroni |
| 3,967,618 A | 7/1976 | Zaffaroni |
| 3,993,072 A | 11/1976 | Zaffaroni |
| 3,993,073 A | 11/1976 | Zaffaroni |
| 3,995,631 A | 12/1976 | Higuchi et al. |
| 4,018,918 A | 4/1977 | Ayer et al. |
| 4,034,756 A | 7/1977 | Higuchi et al. |
| 4,036,227 A | 7/1977 | Zaffaroni et al. |
| 4,036,360 A | 7/1977 | Deffeyes |
| 4,041,208 A | 8/1977 | Seeger et al. |
| 4,093,708 A | 6/1978 | Zaffaroni et al. |
| 4,096,238 A | 6/1978 | Zaffaroni et al. |
| 4,098,747 A | 7/1978 | Bailey et al. |
| 4,135,514 A | 1/1979 | Zaffaroni et al. |
| 4,142,526 A | 3/1979 | Zaffaroni et al. |
| 4,202,880 A | 5/1980 | Fildes et al. |
| 4,205,115 A | 5/1980 | Piccirilli et al. |
| 4,215,691 A | 8/1980 | Wong |
| 4,235,988 A | 11/1980 | Fildes et al. |
| 4,237,885 A | 12/1980 | Wong |
| 4,250,611 A | 2/1981 | Wong |
| 4,264,757 A | 4/1981 | Park |
| 4,276,405 A | 6/1981 | Koleske et al. |
| 4,286,587 A | 9/1981 | Wong |
| 4,289,757 A | 9/1981 | Glenn |

(Continued)

FOREIGN PATENT DOCUMENTS

| | | |
|---|---|---|
| DE | 19842636 | 3/1999 |
| DE | 19742217 | 4/1999 |

(Continued)

OTHER PUBLICATIONS

J.P. Santerre, K. Woodhouse, G. Laroche, R.S. Labow. Understanding the biodegradation of polyurethanes: From classical implants to tissue engineering materials. Biomaterials 26(35), Dec. 2005: 7457-7470.*

Angel Leiva, Alejandro Farias, Ligia Gargallo, Deodato Radic. Poly($\epsilon$-caprolactone)-block-poly(ethyleneoxide)-block-poly($\epsilon$-caprolactone): Biodegradable triblock copolymer spread at the air-water interface. European Polymer Journal 44(8), Aug. 2008:2589-2598.*

Shaobing Zhou, Xianmo Deng, Hua Yang. Biodegradable poly($\epsilon$-caprolactone)-poly(ethylene glycol) block copolymers: characterization and their use as drug carriers for a controlled delivery system. Biomaterials (2003) 24(20): 3563-3570.*

(Continued)

*Primary Examiner* — Robert A Wax
*Assistant Examiner* — Olga V Tcherkasskaya
(74) *Attorney, Agent, or Firm* — Fish & Richardson P.C.

(57) ABSTRACT

A bioresorbable polymer is obtained by reacting together (a) a prepolymer comprising co-polymerised units of a caprolactone and poly(alkylene oxide) moieties; (b) a polycaprolactone diol comprising co-polymerised units of a caprolactone and a $C_2$-$C_6$ diol; and (c) a diisocyanate. The polymer may be loaded with a pharmaceutically active agent to produce a drug delivery device.

38 Claims, 2 Drawing Sheets

(56) References Cited

U.S. PATENT DOCUMENTS

| | | |
|---|---|---|
| 4,327,727 A | 5/1982 | Prahl et al. |
| 4,379,915 A | 4/1983 | Watanabe et al. |
| 4,402,695 A | 9/1983 | Wong |
| 4,404,296 A | 9/1983 | Schapel |
| 4,426,485 A | 1/1984 | Hoy et al. |
| 4,438,225 A | 3/1984 | Peerman |
| 4,447,591 A | 5/1984 | Watanabe et al. |
| 4,466,936 A | 8/1984 | Schapel |
| 4,503,216 A | 3/1985 | Fagerburg et al. |
| 4,568,741 A | 2/1986 | Livingston |
| 4,594,240 A | 6/1986 | Kawata et al. |
| 4,596,576 A | 6/1986 | de Nijs |
| 4,647,596 A | 3/1987 | Ishii et al. |
| 4,694,238 A | 9/1987 | Norton |
| 4,707,495 A | 11/1987 | Rosenthale et al. |
| 4,731,289 A | 3/1988 | Coleman |
| 4,767,787 A | 8/1988 | Kawata et al. |
| 4,804,691 A | 2/1989 | English et al. |
| 4,814,182 A | 3/1989 | Graham et al. |
| 4,818,517 A | 4/1989 | Kwee et al. |
| 4,894,238 A | 1/1990 | Embry et al. |
| 4,895,934 A | 1/1990 | Matier et al. |
| 4,917,686 A | 4/1990 | Bayston et al. |
| 4,931,288 A | 6/1990 | Embrey et al. |
| 4,933,418 A | 6/1990 | Sterrett |
| 4,940,588 A | 7/1990 | Sparks et al. |
| 4,945,149 A | 7/1990 | Matsumoto et al. |
| 4,952,402 A | 8/1990 | Sparks et al. |
| 4,954,043 A | 9/1990 | Yoshida et al. |
| 4,973,304 A | 11/1990 | Graham et al. |
| 5,000,955 A | 3/1991 | Gould et al. |
| 5,002,540 A | 3/1991 | Brodman et al. |
| 5,017,382 A | 5/1991 | Embrey et al. |
| 5,023,252 A | 6/1991 | Hseih |
| 5,035,891 A | 7/1991 | Runkel et al. |
| 5,045,622 A | 9/1991 | Kohno et al. |
| 5,049,638 A | 9/1991 | Matsumoto et al. |
| 5,055,516 A | 10/1991 | Fisch et al. |
| 5,057,573 A | 10/1991 | Pascault et al. |
| 5,061,254 A | 10/1991 | Karakelle et al. |
| 5,079,009 A | 1/1992 | Embrey et al. |
| 5,100,926 A | 3/1992 | Kondo et al. |
| 5,110,598 A | 5/1992 | Kwan et al. |
| 5,114,718 A | 5/1992 | Damani |
| 5,116,932 A | 5/1992 | Fujiwa |
| 5,118,779 A | 6/1992 | Szycher |
| 5,130,126 A | 7/1992 | Koyama et al. |
| 5,134,151 A | 7/1992 | Bartroli et al. |
| 5,156,900 A | 10/1992 | Nishimura |
| 5,159,047 A | 10/1992 | Simms |
| 5,176,907 A | 1/1993 | Leong |
| 5,178,874 A | 1/1993 | Kwan et al. |
| 5,219,663 A | 6/1993 | Kohno et al. |
| 5,219,885 A | 6/1993 | Frolich et al. |
| 5,252,602 A | 10/1993 | Alam et al. |
| 5,269,321 A | 12/1993 | MacDonald et al. |
| 5,283,297 A | 2/1994 | Miyachi et al. |
| 5,310,759 A | 5/1994 | Bockman |
| 5,312,865 A | 5/1994 | Hoefer et al. |
| 5,322,063 A | 6/1994 | Allen et al. |
| 5,324,746 A | 6/1994 | McKee et al. |
| 5,326,632 A | 7/1994 | Zenda et al. |
| 5,328,954 A | 7/1994 | Sarangapani |
| 5,354,556 A | 10/1994 | Sparks et al. |
| 5,374,704 A | 12/1994 | Muller et al. |
| 5,464,868 A | 11/1995 | Frolich et al. |
| 5,470,829 A | 11/1995 | Prisell et al. |
| 5,472,785 A | 12/1995 | Stobbie, IV et al. |
| 5,474,767 A | 12/1995 | Tremont |
| 5,505,962 A | 4/1996 | Sparks |
| 5,510,384 A | 4/1996 | McKee et al. |
| 5,514,698 A | 5/1996 | Ahmad et al. |
| 5,527,534 A | 6/1996 | Myhling |
| 5,574,102 A | 11/1996 | Tanigami et al. |
| 5,578,640 A | 11/1996 | Hanson |
| 5,578,643 A | 11/1996 | Hanson |
| 5,605,931 A | 2/1997 | Hanson |
| 5,627,254 A | 5/1997 | Oriani |
| 5,634,895 A | 6/1997 | Igo et al. |
| 5,650,171 A | 7/1997 | Quigley, Jr. et al. |
| 5,652,274 A | 7/1997 | Martin |
| 5,659,003 A | 8/1997 | Menovcik et al. |
| 5,676,939 A | 10/1997 | Tremont |
| 5,681,278 A | 10/1997 | Igo et al. |
| 5,681,850 A | 10/1997 | Frolich et al. |
| 5,686,425 A | 11/1997 | Lee |
| 5,693,319 A | 12/1997 | Tremont |
| 5,700,483 A | 12/1997 | Quigley, Jr. et al. |
| 5,710,215 A | 1/1998 | Abend |
| 5,716,676 A | 2/1998 | Schutze et al. |
| 5,723,552 A | 3/1998 | Menovcik et al. |
| 5,726,244 A | 3/1998 | McGee et al. |
| 5,726,274 A | 3/1998 | Menovcik et al. |
| 5,731,303 A | 3/1998 | Hsieh |
| 5,733,538 A | 3/1998 | Riffle |
| 5,739,113 A | 4/1998 | Lee |
| 5,744,550 A | 4/1998 | Menovcik et al. |
| 5,747,058 A | 5/1998 | Tipton et al. |
| 5,747,582 A | 5/1998 | Schutze et al. |
| 5,760,127 A | 6/1998 | Bammel et al. |
| 5,763,399 A | 6/1998 | Lee |
| 5,770,650 A | 6/1998 | McGee et al. |
| 5,777,048 A | 7/1998 | Ohrbom et al. |
| 5,780,049 A | 7/1998 | Deckner et al. |
| 5,792,810 A | 8/1998 | Menovcik et al. |
| 5,795,567 A | 8/1998 | Tremont |
| 5,817,343 A | 10/1998 | Burke |
| 5,827,925 A | 10/1998 | Tremont et al. |
| 5,827,930 A | 10/1998 | Ohrbom et al. |
| 5,827,931 A | 10/1998 | Menovcik et al. |
| 5,843,961 A | 12/1998 | Kock et al. |
| 5,849,803 A | 12/1998 | Kock et al. |
| 5,853,767 A | 12/1998 | Melman |
| 5,854,385 A | 12/1998 | McGee et al. |
| 5,855,906 A | 1/1999 | McClay |
| 5,872,195 A | 2/1999 | Green et al. |
| 5,877,216 A | 3/1999 | Place et al. |
| 5,886,039 A | 3/1999 | Kock et al. |
| 5,888,930 A | 3/1999 | Smith et al. |
| 5,891,915 A | 4/1999 | Wysor et al. |
| 5,897,879 A | 4/1999 | Friedman et al. |
| 5,900,433 A | 5/1999 | Igo et al. |
| 5,935,939 A | 8/1999 | Kararli et al. |
| 5,942,512 A | 8/1999 | Kock et al. |
| 5,942,545 A | 8/1999 | Samour et al. |
| 5,948,416 A | 9/1999 | Wagner et al. |
| 5,959,775 A | 9/1999 | Joseph et al. |
| 5,965,662 A | 10/1999 | Krebs et al. |
| 5,968,542 A | 10/1999 | Tipton |
| 5,972,372 A | 10/1999 | Saleh et al. |
| 5,973,002 A | 10/1999 | Frolich et al. |
| 5,977,172 A | 11/1999 | Yoshikawa et al. |
| 5,985,859 A | 11/1999 | Luo |
| 5,994,479 A | 11/1999 | Green et al. |
| 5,994,492 A | 11/1999 | Graham et al. |
| 6,008,312 A | 12/1999 | Shirasaka |
| 6,013,637 A | 1/2000 | Klein et al. |
| 6,022,554 A | 2/2000 | Lee et al. |
| 6,028,057 A | 2/2000 | Burns |
| 6,031,002 A | 2/2000 | Wysor et al. |
| 6,039,968 A | 3/2000 | Nabahi |
| 6,040,062 A | 3/2000 | McGee et al. |
| 6,043,224 A | 3/2000 | Lee et al. |
| 6,046,244 A | 4/2000 | Buyuktimkin et al. |
| 6,080,825 A | 6/2000 | Ohrbom et al. |
| 6,084,038 A | 7/2000 | Ohrbom et al. |
| 6,086,909 A | 7/2000 | Harrison et al. |
| 6,093,270 A | 7/2000 | Ferencz et al. |
| 6,103,256 A | 8/2000 | Nabahi |
| 6,103,765 A | 8/2000 | Neal |
| 6,103,852 A | 8/2000 | Shirasaka |
| 6,114,444 A | 9/2000 | Rehfuss et al. |
| 6,117,024 A | 9/2000 | Dewanjee |
| 6,117,843 A | 9/2000 | Baroody et al. |

| | | | | | | |
|---|---|---|---|---|---|---|
| 6,123,963 A | 9/2000 | Kim et al. | | 7,883,718 B2 | 2/2011 | Ron et al. |
| 6,126,958 A | 10/2000 | Saleh et al. | | 7,892,163 B2 | 2/2011 | Bartning et al. |
| 6,130,200 A | 10/2000 | Brodbeck et al. | | 2001/0014715 A1 | 8/2001 | Blum et al. |
| 6,130,309 A | 10/2000 | Reich et al. | | 2001/0044467 A1 | 11/2001 | Neal |
| 6,140,453 A | 10/2000 | Julia Barges et al. | | 2001/0051656 A1 | 12/2001 | Place et al. |
| 6,150,489 A | 11/2000 | Pudleiner et al. | | 2001/0051694 A1 | 12/2001 | Julia Barges et al. |
| 6,160,058 A | 12/2000 | Ohrbom et al. | | 2002/0004529 A1 | 1/2002 | Neal |
| 6,184,248 B1 | 2/2001 | Lee et al. | | 2002/0013304 A1 | 1/2002 | Wilson et al. |
| 6,187,756 B1 | 2/2001 | Lee et al. | | 2002/0028846 A1 | 3/2002 | Yeager et al. |
| 6,188,039 B1 | 2/2001 | Gass | | 2002/0037491 A1 | 3/2002 | Halliday et al. |
| 6,197,327 B1 | 3/2001 | Harrison et al. | | 2002/0039935 A1 | 4/2002 | Dewanjee |
| 6,210,343 B1 | 4/2001 | Kanakaris et al. | | 2002/0045665 A1 | 4/2002 | Yeager et al. |
| 6,210,441 B1 | 4/2001 | Flodin | | 2002/0052407 A1 | 5/2002 | Lee et al. |
| 6,221,997 B1 | 4/2001 | Woodhouse et al. | | 2002/0062097 A1 | 5/2002 | Simpson |
| 6,284,836 B1 | 9/2001 | Hassel et al. | | 2002/0077442 A1 | 6/2002 | Gertzmann et al. |
| 6,294,550 B1 | 9/2001 | Place et al. | | 2002/0077444 A1 | 6/2002 | Matsumoto et al. |
| 6,303,147 B1 | 10/2001 | Gilis | | 2002/0099003 A1 | 7/2002 | Wilson et al. |
| 6,303,606 B1 | 10/2001 | Leonardi et al. | | 2002/0115814 A1 | 8/2002 | Woodhouse et al. |
| 6,306,841 B1 | 10/2001 | Place et al. | | 2002/0115976 A1 | 8/2002 | Fleming |
| 6,323,241 B1 | 11/2001 | Yeager et al. | | 2002/0119833 A1 | 8/2002 | Dewanjee |
| 6,328,991 B1 | 12/2001 | Myhling | | 2002/0128314 A1 | 9/2002 | Neal |
| 6,335,003 B1 | 1/2002 | Kim et al. | | 2002/0132965 A1 | 9/2002 | Gertzmann et al. |
| 6,346,599 B1 * | 2/2002 | Goldberg et al. ............. 528/354 | | 2002/0161009 A1 | 10/2002 | Leonardi et al. |
| 6,359,100 B1 | 3/2002 | Hostettler et al. | | 2003/0022022 A1 | 1/2003 | Kizumoto et al. |
| 6,403,665 B1 | 6/2002 | Sieker et al. | | 2003/0032754 A1 | 2/2003 | Kaufhold et al. |
| 6,410,595 B1 | 6/2002 | Neal | | 2003/0032759 A1 | 2/2003 | Fischer et al. |
| 6,413,536 B1 | 7/2002 | Gibson et al. | | 2003/0045668 A1 | 3/2003 | Fischer et al. |
| 6,414,027 B1 | 7/2002 | Neal | | 2003/0060589 A1 | 3/2003 | Shimizu et al. |
| 6,414,028 B1 | 7/2002 | Buyuktimkin et al. | | 2003/0122282 A1 | 7/2003 | Plummer et al. |
| 6,416,779 B1 | 7/2002 | D'Augustine et al. | | 2003/0129241 A1 | 7/2003 | Yeager et al. |
| 6,420,510 B1 | 7/2002 | Kaufhold et al. | | 2003/0134903 A1 | 7/2003 | Yeager et al. |
| 6,423,788 B1 | 7/2002 | Bammel et al. | | 2003/0144454 A1 | 7/2003 | Krebs et al. |
| 6,440,568 B1 | 8/2002 | Kayanoki et al. | | 2003/0158369 A1 | 8/2003 | Slagel |
| 6,469,016 B1 | 10/2002 | Place et al. | | 2003/0207852 A1 | 11/2003 | Place et al. |
| 6,469,055 B2 | 10/2002 | Lee et al. | | 2003/0212139 A1 | 11/2003 | Neal |
| 6,471,955 B1 | 10/2002 | Tremont et al. | | 2004/0014761 A1 | 1/2004 | Place et al. |
| 6,472,434 B1 | 10/2002 | Place et al. | | 2004/0044080 A1 | 3/2004 | Place et al. |
| 6,482,345 B1 | 11/2002 | Dewanjee | | 2004/0047910 A1 | 3/2004 | Beckett et al. |
| 6,486,207 B2 | 11/2002 | Yeager et al. | | 2004/0110843 A1 | 6/2004 | Yeager et al. |
| 6,488,953 B2 | 12/2002 | Halliday et al. | | 2004/0115229 A1 | 6/2004 | Roby |
| 6,495,157 B1 | 12/2002 | Pena et al. | | 2004/0131664 A1 | 7/2004 | Mo et al. |
| 6,511,388 B1 | 1/2003 | Dewanjee | | 2004/0142847 A1 | 7/2004 | Bayersdoerfer et al. |
| 6,512,073 B2 | 1/2003 | Gertzmann et al. | | 2004/0157766 A1 | 8/2004 | Embil et al. |
| 6,521,164 B1 | 2/2003 | Plummer et al. | | 2004/0265355 A1 | 12/2004 | Shalaby |
| 6,537,970 B1 | 3/2003 | Vulpescu et al. | | 2004/0266688 A1 | 12/2004 | Nayak |
| 6,543,828 B1 | 4/2003 | Gass | | 2005/0004226 A1 | 1/2005 | Lu et al. |
| 6,545,119 B2 | 4/2003 | Kizumoto et al. | | 2005/0013793 A1 | 1/2005 | Beckman et al. |
| 6,559,184 B2 | 5/2003 | Neal | | 2005/0031690 A1 | 2/2005 | Rohrs et al. |
| 6,572,874 B1 | 6/2003 | Harrison et al. | | 2005/0048104 A1 | 3/2005 | Venkatraman et al. |
| 6,586,553 B1 | 7/2003 | Muhlfeld et al. | | 2005/0053639 A1 | 3/2005 | Shalaby |
| 6,589,990 B1 | 7/2003 | Kanakaris et al. | | 2005/0053670 A1 | 3/2005 | Schaub |
| 6,592,472 B2 | 7/2003 | Dewanjee | | 2005/0070516 A1 | 3/2005 | Wilson et al. |
| 6,593,313 B2 | 7/2003 | Place et al. | | 2005/0090474 A1 | 4/2005 | Naor |
| 6,593,369 B2 | 7/2003 | Neal | | 2005/0095245 A1 | 5/2005 | Riley et al. |
| 6,607,686 B2 | 8/2003 | Dewanjee | | 2005/0161030 A1 | 7/2005 | Robert et al. |
| 6,630,050 B1 | 10/2003 | Moeller et al. | | 2005/0169975 A1 | 8/2005 | Suzuki et al. |
| 6,632,913 B2 | 10/2003 | Matsumoto et al. | | 2005/0181030 A1 | 8/2005 | Mo et al. |
| 6,641,064 B1 | 11/2003 | Dentler et al. | | 2005/0187342 A1 | 8/2005 | Schieferstein et al. |
| 6,642,274 B1 | 11/2003 | Neal | | 2005/0208152 A1 | 9/2005 | Milankovits |
| 6,664,290 B1 | 12/2003 | El-Rafaey | | 2005/0238722 A1 * | 10/2005 | Pathak et al. .................. 424/486 |
| 6,693,135 B2 | 2/2004 | Yeager et al. | | 2005/0245902 A1 | 11/2005 | Cornish et al. |
| 6,740,333 B2 | 5/2004 | Beckett et al. | | 2006/0003950 A1 | 1/2006 | Strugnell et al. |
| 6,790,926 B1 | 9/2004 | Spijkers et al. | | 2006/0018951 A1 | 1/2006 | Maniar et al. |
| 6,794,372 B2 | 9/2004 | Del Soldato et al. | | 2006/0041021 A1 | 2/2006 | Wilson et al. |
| 6,825,234 B2 | 11/2004 | Yeager et al. | | 2006/0052341 A1 | 3/2006 | Cornish et al. |
| 6,841,574 B2 | 1/2005 | Mo et al. | | 2006/0078616 A1 | 4/2006 | Georgewill et al. |
| 6,861,503 B2 * | 3/2005 | Shalaby ........................ 528/425 | | 2006/0093675 A1 | 5/2006 | Ebmeier et al. |
| 6,953,800 B2 | 10/2005 | Leonardi et al. | | 2006/0134161 A1 | 6/2006 | Halliday |
| 6,992,161 B1 | 1/2006 | Kim et al. | | 2006/0183724 A1 | 8/2006 | Diliberti et al. |
| 7,053,209 B1 | 5/2006 | Gibson et al. | | 2006/0210599 A1 | 9/2006 | Gibson et al. |
| 7,179,481 B2 | 2/2007 | Villanueva | | 2007/0043332 A1 | 2/2007 | Malcolm et al. |
| 7,485,666 B2 | 2/2009 | Villanueva et al. | | 2007/0128154 A1 * | 6/2007 | Hadba et al. ................ 424/78.27 |
| 7,670,606 B2 | 3/2010 | Volkmann | | 2007/0135605 A1 * | 6/2007 | Hadba et al. ................... 528/44 |
| 7,717,892 B2 | 5/2010 | Bartning | | 2007/0148105 A1 | 6/2007 | Spector |
| 7,795,467 B1 | 9/2010 | Pacetti et al. | | 2007/0155906 A1 * | 7/2007 | Hissink et al. ................. 525/242 |
| 7,829,112 B2 | 11/2010 | Ron et al. | | 2007/0166382 A1 * | 7/2007 | Kiser et al. ..................... 424/486 |
| 7,833,543 B2 | 11/2010 | Gibson et al. | | 2007/0282093 A1 | 12/2007 | Yoshimura et al. |
| 7,833,545 B2 | 11/2010 | Ron et al. | | 2008/0009663 A1 | 1/2008 | Bartning et al. |
| 7,838,024 B2 | 11/2010 | Ron et al. | | 2008/0009666 A1 | 1/2008 | Bartning et al. |

| | | |
|---|---|---|
| 2008/0108775 A1 | 5/2008 | Schieferstein et al. |
| 2008/0140185 A1 | 6/2008 | Kiser et al. |
| 2008/0145419 A1 | 6/2008 | Gibson et al. |
| 2008/0152708 A1 | 6/2008 | Gibson et al. |
| 2008/0199511 A1 | 8/2008 | Sitruk-Ware et al. |
| 2008/0206310 A1 | 8/2008 | Davis |
| 2008/0207571 A1 | 8/2008 | Davis |
| 2008/0262613 A1 | 10/2008 | Gogolewski |
| 2008/0271190 A1 | 10/2008 | Holland |
| 2008/0286339 A1 | 11/2008 | Ron et al. |
| 2009/0004246 A1 | 1/2009 | Woolfson et al. |
| 2009/0011209 A1 | 1/2009 | Steinberger et al. |
| 2009/0060982 A1 | 3/2009 | Ron et al. |
| 2009/0061172 A1 | 3/2009 | Hayashi et al. |
| 2009/0081278 A1 | 3/2009 | De Graaff et al. |
| 2009/0203591 A1 | 8/2009 | Bagchi et al. |
| 2009/0203772 A1 | 8/2009 | Villanueva et al. |
| 2009/0291120 A1 | 11/2009 | Tuominen et al. |
| 2010/0104619 A1 | 4/2010 | De Graaff et al. |
| 2010/0203104 A1 | 8/2010 | De Graaff et al. |
| 2010/0285094 A1 | 11/2010 | Gupta |
| 2011/0045076 A1 | 2/2011 | Kiser et al. |
| 2011/0056501 A1 | 3/2011 | Kortesuo et al. |
| 2011/0059040 A1 | 3/2011 | Kiser et al. |
| 2011/0077578 A1 | 3/2011 | Bartning et al. |
| 2011/0091488 A1 | 4/2011 | Halliday et al. |
| 2011/0150955 A1 | 6/2011 | Klingman |

FOREIGN PATENT DOCUMENTS

| | | |
|---|---|---|
| EP | 335669 | 3/1989 |
| EP | 0401990 | 5/1990 |
| EP | 424164 | 10/1990 |
| EP | 0450176 | 10/1991 |
| EP | 0401990 | 1/1992 |
| EP | 1063942 | 6/2004 |
| FR | 2557576 | 7/1985 |
| FR | 2705567 | 12/1994 |
| GB | 2047093 | 11/1980 |
| GB | 2047094 | 11/1980 |
| GB | 2244920 | 12/1991 |
| JP | 5600253 | 3/1980 |
| JP | 1135488 | 2/1983 |
| JP | 0670 952 | 3/1994 |
| JP | 1150610 | 6/1999 |
| JP | 200502691 | 3/2000 |
| JP | 2001513550 | 9/2001 |
| JP | 2002515069 | 5/2002 |
| JP | 2011/507405 | 3/2011 |
| WO | WO 80/01984 | 10/1980 |
| WO | 2047094 | 11/1980 |
| WO | 8905319 | 6/1989 |
| WO | 8907117 | 10/1989 |
| WO | 9102763 | 3/1991 |
| WO | 9403510 | 2/1994 |
| WO | 9413724 | 6/1994 |
| WO | 9422934 | 10/1994 |
| WO | 9606875 | 3/1996 |
| WO | 9615171 | 5/1996 |
| WO | WO 96/38153 | 5/1996 |
| WO | 9621427 | 7/1996 |
| WO | 9631551 | 10/1996 |
| WO | 9717386 | 5/1997 |
| WO | 9724109 | 7/1997 |
| WO | WO 97/24109 | 7/1997 |
| WO | WO 98/56323 | 12/1998 |
| WO | WO 99/09964 | 3/1999 |
| WO | 9947073 | 9/1999 |
| WO | 9947127 | 9/1999 |
| WO | 9956731 | 11/1999 |
| WO | 0000222 | 1/2000 |
| WO | 0040222 | 7/2000 |
| WO | WO 00/40222 | 7/2000 |
| WO | WO 02/03896 | 1/2002 |
| WO | WO 02/09631 | 2/2002 |
| WO | 03011301 | 2/2003 |
| WO | 03087183 | 10/2003 |
| WO | 2004029125 | 4/2004 |
| WO | 2004084872 | 10/2004 |
| WO | 2005068533 | 7/2005 |
| WO | WO 2005/063145 | 7/2005 |
| WO | 2005089778 | 9/2005 |
| WO | 2005116100 | 12/2005 |
| WO | 2006013335 | 2/2006 |
| WO | 2006048639 | 5/2006 |
| WO | 2006048639 | 11/2006 |
| WO | 2008007098 | 1/2008 |
| WO | 2009094573 | 7/2009 |
| WO | WO 10/35837 | 4/2010 |
| WO | WO 2010/119029 | 5/2010 |
| WO | WO 2011/011099 | 1/2011 |
| WO | WO 2011/039418 | 4/2011 |

OTHER PUBLICATIONS

Jianzhong et al. Polycaprolactone-poly(ethylene glycol) block copolymer III Drug release behavior. Chinese J Polym Sci., 13(2) 1995:154:161.*
Lee JW, Hua F, Lee DS. Thermoreversible gelation of biodegradable poly(epsilon-caprolactone) and poly(ethylene glycol) multiblock copolymers in aqueous solutions. J Control Release. Jun. 15, 2001;73(2-3):315-27.*
Gustavo A Abraham, Angel Marcos-Fernández, Julio San Román. Bioresorbable poly(ester-ether urethane)s from L-lysine diisocyanate and triblock copolymers with different hydrophilic character. Journal of Biomedical Materials Research Part A (2006) 76(4): 729-736.*
Baimak et al. Synthesis and characterization of poly(l-lactide-co-e-caprolactone) copolymers: Effect of stannous octoate initiator and diethylel glycol coinitiator concentration. ScienceAsia 30 (2004):324-334.*
PCTGB2007 002401 Written Opinion of International Searching Authority Oct. 24, 2007.
PCTGB2007 002401 International Search Report Oct. 24, 2007.
PCTGB207 002604 International Search Report Jul. 12, 2007.
PCTGB207 002604 Written Opinion of International Searching Authority Jul. 12, 2007.
PCTGB2005 002951 International Preliminary Report on Patentability Feb. 6, 2007.
PCTGB2005 002951 International Search Report Oct. 20, 2005.
PCTGB2003 004208 International Search Report Jan. 2, 2004.
PCTGB2007 002415 International Search Report Oct. 30, 2007.
PCTGB2007 002415 Written Opinion of International Searching Authority Oct. 30, 2007.
PCTGB2005 002951 Written Opinion of International Searching Authority Oct. 20, 2005.
Abraham, Gustavo A. et al "Bioresorbable poly(ester-ether urethane)s from L-lysine diisocyanate and triblock copolymers with different hydrophilic character" Wiley Periodicals, Inc. 2005.
Yu, J. et al "Blood interactions with novel polyurethaneurea hydrogels" Biomaterials 1991.
Casteneda, C.S. et al "Misoprostol Dose Selection in a controlled-release vaginal insert for induction of labor in nulliparous women" AJOG, Sep. 2005.
Tyagi, P. et al "Sustained Intravesical Drug Delivery Using Thermosensitive Hydrogel" Pharmaceutical Research May 2004.
Merck Index (Ninth Edition, 1976, p. 4073).
Chen, "Stabilization and sustained-release effect of Misoprostol with Methacrylate copolymer", International Journal of Pharmaceutics, 203 (2000) pp. 141-148.
Kararli, "Stabilization of Misoprostol with Hydroxypropyl Methylcellulose (HMPC) Against Degradation by Water", Pharmaceutical Research, vol. 7, No. 11 (1990).
PCT/GB207/002604, International Search Report, dated Jul. 12, 2007.
Sato et al., "The effects of a prostaglandin El analogue, misoprostol, on gastric mucosal blood volume index and haemoglobin oxygenation in humans", Journal of Gastroenterology and Hepatology, 2008, 2(6), 499-505.

* cited by examiner

BIORESORBABLE POLYMERS

This application is a national stage filing under 35 U.S.C. §371 of International Application PCT/GB2007/003936, filed Oct. 15, 2007, which claims priority from United Kingdom Application GB 0620685.8, filed Oct. 18, 2006, the entireties of each of which are hereby incorporated by reference. International Application PCT/GB2007/003936 was published under PCT Article 21(2) in English.

FIELD OF THE INVENTION

The present invention relates to bioresorbable polymers derived from structural units comprising caprolactone, polyols and diisocyanates, and the manufacture of the bioresorbable polymers.

BACKGROUND OF THE INVENTION

Bioresorbable and/or biodegradable polymers (i.e. biopolymers) can be divided into natural and synthetic polymers. To the natural polymers belong e.g. proteins, polysaccharides and lignin. Synthetic biopolymers are e.g. aliphatic polyesters, polyorthoesters, some aliphatic polycarbonates, polyanhydrides and some polyurethanes. Biopolymers can also be produced by microbes e.g. polyhydroxy alkanoates. The most important group of biodegradable polymers is based on aliphatic polyesters, the degradation of which is mainly based on hydrolysable ester bonds. Bioresorbable polymers degrade in the physiological environment and the degradation products are eliminated through the kidneys or completely bioabsorbed. According to strict definition, biodegradable polymers require enzymes or micro-organisms for hydrolytic or oxidative degradation. But in general, a polymer that loses its mass over time in the living body is called an absorbable, resorbable, bioresorbable or biodegradable polymer. This terminology is applied in the present invention regardless of polymer degradation mode, in other words for both enzymatic and non-enzymatic degradation and/or erosion.

Biodegradable polymers are used and studied in an increasingly large number of biomedical applications, such as controlled drug delivery devices, implants and resorbable sutures, as well as mass produced applications such as packaging, paper coating, fibres, films and other disposable articles. These applications bring special requirements to the polymers and monomers. These polymers are generally required to be biodegradable and non-toxic, or in the biomedical applications, bioresorbable and/or biocompatible. On the other hand, polymers should have good chemical, mechanical, thermal and rheological properties.

In the last few decades, novel controlled drug delivery systems have attracted interest due to their potential advantages. For example, the safety and efficacy of many drugs can be improved if they are administered by novel delivery systems. For many drugs a constant plasma concentration is desirable, especially for those drugs exhibiting narrow therapeutic indexes. Bioabsorbable devices represent the state of the art in drug delivery and in managing orthopaedic problems such as the use of implants in fracture fixation and ligament repair. Biodegradable polymers applied as drug delivery systems generally require no follow-up surgical removal once the drug supply has been depleted. Mainly implantable rods, microspheres and pellets have been investigated.

Polycaprolactone (PCL) is among the most common and well-studied bioresorbable polymer. The repeating molecular structure of PCL homopolymer consists of five non-polar methylene groups and a single relatively polar ester group. This high molecular weight polyester is conventionally produced by the ring-opening polymerisation of the cyclic monomer, i.e. ε-caprolactone. A catalyst is used to start the polymerisation and an initiator, such as an alcohol, can be used to control the reaction rate and to adjust the average molecular weight. PCL is a semi-crystalline (~40-50%), strong, ductile and hydrophobic polymer with excellent mechanical characteristics having a low melting point of 60° C. and a glass transition temperature of −60° C.

Poly(ethylene glycol) is a biocompatible and highly water soluble (hydrophilic) polymer. Poly(ethylene glycols) are low molecular weight (<20000 g/mol) poly(ethylene oxides) containing the repeat unit —$CH_2CH_2O$—. PEG is a highly crystalline (~90-95%) polymer having a low melting point of 60° C. and a glass transition temperature of −55 to −70° C. These difunctional compounds contain hydroxyl end-groups, which can be further reacted and chain extended with diisocyanates or used as initiators for ring-opening polymerisations. PEGs are well-known structural units incorporated into crosslinked polyurethane hydrogels (EP publications EP0016652 and EP0016654) and linear polyurethane hydrogels (PCT publication WO2004029125).

Amphiphilic block copolymers, e.g. PEG-PCL copolymers, have recently attracted attention in the field of medicine and biology as micellar carriers, polymer vesicles and polymer matrices. The triblock copolymer PCL-PEG-PCL has unique phase behaviour in blends and the ability to form polymeric micelle-like core-shell nanostructures in a selective solvent, in which only one block is soluble (*J. Polym. Sci. Part A Polym. Chem.*, 1997, 35, 709-714; *Adv. Drug Delivery Rev.*, 2001, 53, 95-108).

However, the above-mentioned polymers suffer from a number of practical disadvantages. The degradation rate and mechanism appear to depend on a number of factors, such as the chemical structure of the polymer and on the surrounding environmental conditions, such as the degradation media. Two stages have been identified in the degradation process of aliphatic polyesters. Initially, the degradation proceeds by random hydrolytic chain scission of the ester bonds, leading to a decrease in the molecular weight; in the second stage measurable weight loss in addition to chain scission is observed. Another observation is that polycaprolactone degrades much slower than e.g. polylactide. The long degradation time of polycaprolactone (~24 months) is usually a disadvantage for medical applications.

It is an object of the present invention to obviate and/or mitigate the disadvantages of the known bioresorbable polymers. In particular, it is an object of the present invention to provide a consistent and/or flexible approach to providing polymers having differing degradation properties which may be chosen according to the intended use of the polymers, including providing polymers having differing degradation rates. It is a further object to provide bioresorbable polyurethane polymers which fulfil one or more of these objects. A preferable object is to provide bioresorbable polyurethane polymers which are non-toxic on degradation.

SUMMARY OF THE INVENTION

According to a first aspect of the present invention, there is provided a polymer obtainable by reacting together:
(a) a prepolymer comprising co-polymerised units of a caprolactone and poly(alkylene oxide) moieties;
(b) a polycaprolactone diol comprising co-polymerised units of a caprolactone and a $C_2$-$C_6$ diol; and (c) a diisocyanate.

Alternatively stated, the invention provides a polymer comprising moieties derived from the stated components (a), (b) and (c) bonded together.

Preferably, the poly(alkylene oxide) moieties of the prepolymer (component (a)), are selected from a poly($C_2$-$C_3$ alkylene oxide) or mixtures thereof. Most preferred is a poly($C_2$ alkylene oxide), e.g. derived from a poly($C_2$ alkylene oxide) diol, i.e. poly(ethylene oxide) diols, for example poly(ethylene glycols). Generally and desirably, the poly(alkylene oxide) moieties should be water soluble to assist in the degradation of the subject polymers in aqueous environments.

Poly(ethylene glycols), which are an example of a polyethylene oxide, may be prepared by the addition of ethylene oxide to ethylene glycol to produce a difunctional polyethylene glycol having the structure HO($CH_2CH_2O$)$_n$H wherein n is an integer from 1 to 800 depending on the molecular weight. Polyethylene oxides contain the repeat unit ($CH_2CH_2O$) and are conveniently prepared by the stepwise addition of ethylene oxide to a compound containing a reactive hydrogen atom.

The poly(ethylene glycols) used in the present invention are generally linear polyols having an average molecular weight of about 200 g/mol to about 35,000 g/mol, particularly about 300 g/mol to about 10,000 g/mol, especially about 400 g/mol to about 8000 g/mol, for example about 400, 600, 2000, 4000 or 8000 g/mol.

Preferably, therefore, component (a) comprises a co-polymer of caprolactone and a relatively low to middle range molecular weight poly(ethylene glycol).

Component (a) may be made, for example by polymerising together the caprolactone and the polyol comprising poly(alkylene oxide) moieties, to provide a linear dihydroxyl-terminated caprolactone-poly(alkylene oxide) co-polymer for use as a prepolymer in the preparation of the subject polymer.

For example, ε-caprolactone may be reacted, in a ring opening reaction, with a poly(ethylene glycol) to provide a linear dihydroxyl-terminated caprolactone-poly(ethylene glycol) co-polymer for use as a prepolymer in the preparation of the subject polymer.

Such prepolymer typically has an ABA structure e.g. (CAP)$_n$-PEG-(CAP)$_n$, i.e. one having blocks of continuous caprolactone units flanking a PEG unit, e.g. -CAP-CAP-CAP-PEG-CAP-CAP-CAP-, and the average number of continuous units (i.e. the value of n) of caprolactone in each block of the polycaprolactone segments is generally between about 3 to 40, preferably between about 4 to 35, and typically between about 5 to 31, for example, chosen from 5, 9.5 and 31 units.

Typically, in the preparation of component (a), the polymerisation proceeds with the aid of a catalyst. A typical catalyst useful in the polymerisation is stannous octoate.

The skilled person will appreciate that in the preparation of the prepolymer (component (a)), the poly(alkylene oxide) moiety, which as mentioned herein above is preferably a poly(ethylene glycol) (i.e. PEG), may be considered as an initiator. The precise reaction conditions used will be readily determined by those skilled in the art. Other co-monomers, co-polymers, and catalysts in this ring-opening polymerisation may be used, if different properties are desired in the product, such as elasticity, degradation and release rate, and the choice of such other ingredients will be apparent to those of skill in the art.

Generally, in the preparation of the prepolymer, the molar ratio of caprolactone to initiator (e.g. the PEG) is generally in the range from about 2: about 1 up to about 124: about 1, for example about 10: about 1, about 19: about 1 or about 62: about 1.

The $C_2$-$C_6$ diol component of the polycaprolactone diol (component (b)), may be any organic diol having a relatively lower molecular weight compared to the poly(alkylene oxide) moiety contained in the prepolymer diol component (a).

For example, the $C_2$-$C_6$ diol, may be chosen from diols having a structure: HO—($CH_2$)$_m$—OH, wherein m is a number chosen from 2-6, for example, 1,2-ethylene glycol, 1,4-butane diol, 1,5-pentane diol or 1,6-hexane diol.

Alternatively, the $C_2$-$C_6$ diol may be chosen from diols which are low molecular weight polymers or oligomers chosen from poly(alkylene oxide) diols.

Preferably, such poly(alkylene oxide) diol is selected from a poly($C_2$-$C_3$ alkylene oxide) diol or mixtures thereof. Most preferred are low molecular weight poly($C_2$ alkylene oxide) diols, i.e. low molecular weight poly(ethylene oxide) diols, for example low molecular weight poly(ethylene glycols).

Typically, the low molecular weight poly(ethylene glycol) has the following structure: HO—($CH_2CH_2O$)$_n$—H, wherein n is a number chosen from 2 or 3, i.e. low molecular weight polyethylene glycols are preferred. An alternatively preferred diol is ethylene glycol itself (i.e. wherein n is 1).

The most preferred diol is diethylene glycol, i.e. an ethylene glycol dimer, which has the structure HO—$CH_2CH_2$—O—$CH_2CH_2$—OH.

Generally and desirably, the $C_2$-$C_6$ diol should be water soluble to assist in the degradation of the subject polymers in aqueous environments.

The caprolactone moiety of the polycaprolactone diol (component (b)) is preferably derived from ε-caprolactone. Thus, the polycaprolactone diol is preferably derived from ε-caprolactone in a ring opening reaction using the low molecular weight diol as an initiator which itself becomes incorporated into the polycaprolactone diol. For example, such polycaprolactone diol, may be prepared by reacting ε-caprolactone and diethylene glycol in a ring opening reaction to provide a linear dihydroxyl-terminated poly(co-caprolactone-diethylene glycol). A catalyst may be used in the preparation of the polycaprolactone diol. Suitable catalysts include stannous octate, aluminium isopropoxide and/or titanium n-butoxide.

The ratio of caprolactone to low molecular weight diol initiator may be chosen according to principles readily available to the skilled person. Typically, when low molecular weight poly(ethylene glycol) is used as the low molecular weight diol, the ratio of caprolactone:ethylene glycol is of the order of about 4: about 2, and the co-polymer may have the following structure as an example: OH-CAP-CAP-EG-EG-CAP-CAP-OH, where CAP represents the opened caprolactone ring in the appropriate orientation, i.e. the unit —($CH_2$)$_5$C(O)O— or —O(O)C($CH_2$)$_5$— and EG represents an ethylene glycol unit. It will be appreciated that the order and positioning of the CAP units in the co-polymer molecules may vary.

The diisocyanate component (c) is preferably 1,4-butane diisocyanate, 1,6-hexamethylene diioscyanate, or L-lysine diisocyanate etc.

Such diisocyanates are particularly suitable for applications in which toxic degradation products are to be avoided, e.g. in biomedical applications.

1,4-butane diisocyanate is preferred.

Known biomedical and biodegradable polyurethanes usually contain aromatic, cycloaliphatic or aliphatic diisocyanates, which may produce toxic substances or fragments upon degradation. It is generally accepted that, in the degradation of polyurethanes, any unreacted diisocyanate structural units hydrolyze to their corresponding amines. Most of these diamines are known to be toxic, carcinogenic and/or mutagenic. In the international publication WO9964491, the use of the non-toxic 1,4-butane diisocyanate (BDI) is shown in the manufacture of biomedical polyurethanes having a uniform block-length. The Applicant of the present invention considers that the use of 1,4-butane diisocyanate has a number of advantages because on degradation it yields 1,4-butane diamine, also known as putrescine, which is present in mammalian cells. (*J. Polym. Bull.,* 1997, 38, 211-218).

Thus, an additional advantage of at least one embodiment of the present invention is the use of biocompatible starting materials in the manufacture of the polyurethanes, which produce non-toxic, biocompatible polymers and degradation products.

However, in applications in which the toxicity of the degradation products is not as important, any diisocyanate commonly used to form polyurethanes may be used, (including those listed above) and including diisocyanates such as, dicyclohexylmethane-4,4-diisocyanate and diphenylmethane-4,4-diisocyanate.

The bioresorbable polymers of the present invention may degrade in the physiological environment of animals and the degradation products are eliminated through the kidneys or completely bioabsorbed. According to one definition, biodegradable polymers require enzymes or micro-organisms for hydrolytic or oxidative degradation. But in general, a polymer that loses its mass over time in the living body is called an absorbable, resorbable, bioresorbable or biodegradable polymer. This terminology is applied in the present invention regardless of polymer degradation mode, in other words for both enzymatic and non-enzymatic degradation and/or erosion.

As indicated above, the polymerisation process used to manufacture the bioresorbable polymer of the present invention typically involves a ring-opening polymerisation and a polyaddition reaction to obtain high molecular weight poly (block-caprolactone-co-PEG) urethanes. Accordingly, the present invention also extends to the process used to manufacture the polymers.

According to a further aspect of the present invention there is provided a method for preparing a polymer comprising:
(1) providing:
  (a) a prepolymer comprising co-polymerised units of a caprolactone and poly(alkylene oxide) moieties;
  (b) a polycaprolactone diol comprising co-polymerised units of a caprolactone and a $C_2$-$C_6$ diol; and
  (c) a diisocyanate; and
(2) reacting components (a), (b) and (c) together.

In the preparation of the subject polymer, the prepolymer component (a) can be reacted with components (b) and (c) to provide the final polymer. Preferably, the prepolymer is first combined, such as by admixing (for example by blending) with component (b), followed by reaction with component (c) diisocyanate.

The skilled person will appreciate that other modes of operation may be used to produce the polymers.

The component (a) prepolymer is generally produced by polymerising together caprolactone and a poly(alkylene oxide) diol. Preferably a catalyst is used during this to polymerisation reaction. The reaction is preferably conducted in an inert atmosphere, such as under an atmosphere of dry nitrogen gas.

Suitable catalysts include stannous octate, aluminium isopropoxide and/or titanium n-butoxide.

By using different molar ratios of component (a) (prepolymer), component (b) (e.g. poly(co-caprolactone-diethylene glycol) and diisocyanate (e.g. BDI), the phase structure, degradation rate and mechanical properties of the end polymer products may be tailored. The skilled person may judiciously choose the ratios of components and the reaction times, temperatures and other conditions appropriate to provide the final desired polymer product properties.

Generally, the mole ratio of component (a) to component (b) to component (c) is in the range of about 0.15-1.5 to about 1.0 to about 1.0-2.75, particularly about 0.2-1.0 to about 1.0 to about 1.25-2.5. A preferred range is about 0.25-1.0 to about 1.0 to about 2.5.

As described herein above, the present invention typically employs a two-step polymerisation method, which includes a ring-opening polymerisation and chain extending reaction, in the manufacture of the subject bioresorbable polymer. This straightforward two-step process offers a number of versatile possibilities for tailoring the structure and properties of the polymer components (a) and (b), and the final polymer, thus enabling the polymer to be used for a wide variety of purposes.

Numerous monomers and low molecular weight polymers may be introduced during the described steps of the synthesis, either during manufacture of components (a) or (b), or during preparation of the final polymer. Thus, a wide variety of polymer properties may be obtained in the final polymer using the above-mentioned materials by changing the molar composition. The present invention provides a solution to the typical drawbacks encountered with caprolactone/PEG-based copolymers, which include limited structure-property variations, slow degradation and dissolution rates.

Generally, any conventional polymerisation reactor may be used in the manufacture of the polyurethanes presented in the current invention, e.g. batch reactor, continuous stirred tank reactor (CSTR), extruder, reactive injection moulding (RIM), tube reactor, pipe reactor and/or melt mixer. Further processing of these biodegradable polymers can be done by using conventional processing methods suitable for thermoplastic polymers e.g. injection moulding, extrusion, pultrusion, blow moulding, vacuum moulding, solvent casting and other moulding and casting techniques, as well as dispersion, foam and film forming techniques.

As described above, the skilled reader will understand that the present invention is based on the discovery that only a few monomers and polymers appear to fulfil the required demands for tailored, non-toxic bioresorable polymers. Copolymerisation may be used to increase the degradation rate, and the degradation rate of caprolactone copolymers may be altered by varying the structure of the comonomers, the molar composition and the polymer molecular weight. The degradation media may also affect the degradation behaviour.

The polymers in the present invention may usefully be applied as drug delivery devices. The phase behaviour of the polymers consisting of a highly crystalline block and a rubbery block combined with the very hydrophilic and hydrophobic nature of each block makes them desirable as drug delivery systems because the permeability of each individual component or phase for different loaded drugs can differ widely depending on the properties of the particular drug loaded in the polymer. Furthermore, the flexible processes of the invention allow the properties of the polymer to be selected to suit a desired drug, and tailor how the drug is loaded and then released from the polymer. This offers the opportunity to generate a desired release profile for a chosen drug.

The bioresorbable polymers of the present invention may be applied to a wide range of uses, and such uses are included within the scope of the present invention. The polymer may be used as a matrix for drug delivery systems e.g. as drug loaded implants, micro and nanoparticles, micelles, patches, suppositories or contact lenses. Potentially any drug could be loaded into the bioresorbable polymers of the present invention. In addition, the bioresorbable polymer may be used in other biomedical applications such as implants, scaffoldings, nets or resorbable sutures, as well as mass-produced applications such as packaging, paper coating, fibres, films, foams or other disposable articles.

The present invention, therefore, also provides controlled release compositions comprising the bioresorbable polymer together with an active agent. The active agent may be a pharmaceutically active agent for human or animal use. It may also be any agent where sustained release properties (i.e algicides, fertilisers etc.) are required. Such compositions may be provided as pharmaceutical solid dosage forms, including suppositories, pessaries for vaginal use, buccal inserts for oral administration, transdermal patches or films, subcutaneous implants, etc.

The polymers of the present invention may be loaded with an active agent using any of the techniques readily available to the skilled person. One loading method may involve dissolving the polymer in a solution of the active agent and precipitating microparticles using double emulsion techniques. Other conventional processing techniques for processing thermoplastic polymers may also be applied for loading the polymers of the present invention with an active agent. For example, such techniques may include diffusion loading and tablet pressing techniques. Diffusion loading may involve for example uptake of an active agent from a solution contacting the polymer.

Pharmaceutically active agents of particular interest include:

Proteins such as interferon alpha, beta and gamma, insulin, human growth hormone, leuprolide; peptides such as oxytocin antagonists; enzymes and enzyme inhibitors; Benzodiazepines (e.g. midazolam); Anti-migraine agents (e.g. triptophans, ergotamine and its derivatives); Anti-infective agents (e.g. azoles, and treatments for bacterial vaginosis or candida); and opthalmic agents (e.g. latanoprost).

A detailed list of active agent includes $H_2$ receptor antagonist, antimuscarinics, prostaglandin analogue, proton pump inhibitor, aminosalycilate, corticosteroid, chelating agent, cardiac glycoside, phosphodiesterase inhibitor, thiazide, diuretic, carbonic anhydrase inhibitor, antihypertensive, anti-cancer, anti-depressant, calcium channel blocker, analgesic, opioid antagonist, antiplatelet, anticoagulant, fibrinolytic, statin, adrenoceptor agonist, beta blocker, antihistamine, respiratory stimulant, micolytic, expectorant, benzodiazepine, barbiturate, anxiolytic, antipsychotic, tricyclic antidepressant, $5HT_1$ antagonist, opiate, $5HT_1$ agonist, antiemetic, anti-epileptic, dopaminergic, antibiotic, antifungal, anthelmintic, antiviral, antiprotozoal, antidiabetic, insulin, thyrotoxin, female sex hormone, male sex hormone, antioestrogen, hypothalamic, pituitary hormone, posterior pituitary hormone antagonist, antidiuretic hormone antagonist, bisphosphonate, dopamine receptor stimulant, androgen, non-steroidal anti-inflammatory, immuno suppressant local anaesthetic, sedative, antipsioriatic, silver salt, topical antibacterial, vaccine.

The polymers of the present invention degrade in water, aqueous buffer solutions, physiological fluids, soil, compost, sea water and fresh water, and the like over extended time periods. The composition of the polymer and the temperature may cause different degradation rates, which may be readily determined by the skilled person.

Generally, in use, the polymer may be subjected to a temperature of from about 10° C. to about 95° C., preferably from about 25° C. to 45° C., typically from about 30° C. to 38° C., e.g. 37° C.

The time taken for the polymer to fully degrade, i.e. lose all of its mass, may vary widely, e.g. typically of the order of from about one week to 150 weeks (i.e. about 3 years), preferably of from about 2 weeks to about 100 weeks, e.g. from about 2 weeks to about 60 weeks, such as 4 weeks or 52 weeks.

The degradation time can be tailored for the intended final application.

The Applicant has demonstrated that the objectives described herein are fulfilled by the subject polymers, in particular the caprolactone-PEG polyurethane co-polymers.

DETAILED DESCRIPTION OF THE INVENTION

Embodiments of the present invention are described in more detail in the following non-limiting examples, with reference to the drawings, in which.

EXAMPLE 1

Manufacture of Linear Bioresorbable Prepolymers with Different Structure and Block Lengths for Subsequent Polyurethane Synthesis The length of PEG block (400, 600, 2000, 4000 and 8000 g/mol) and caprolactone block (500-3500 g/mol) was changed. The target prepolymer molecular weight was selected to be between 1000-11 000 g/mol. Prepolymer batch sizes were about 500-600 g. The prepolymers were prepared by varying their compositions as follows (see Table 1): Batch A) Prepolymer A made of 273.00 g PEG400 (15.7 mole-%), 418.17 g caprolactone (84.3 mole-%) and 0.528 g tin(II) octoate (0.03 mole-%), targeting a theoretical molecular weight of 1013 g/mol, Batch B) Prepolymer B made of 90.05 g PEG400 (5.0 mole-%), 488.10 g caprolactone (94.97 mole-%) and 0.547 g tin(II) octoate (0.03 mole-%), targeting a theoretical molecular weight of 2568 g/mol, Batch C) Prepolymer C made of 29.95 g PEG400 (1.6 mole-%), 525.48 g caprolactone (98.37 mole-%) and 0.569 g tin(II) octoate (0.03 mole-%), targeting a theoretical molecular weight of 7418 g/mol, Batch D) Prepolymer D made of 122.25 g PEG600 (5.0 mole-%), 441.76 g caprolactone (94.97 mole-%) and 0.495 g tin(II) octoate (0.03 mole-%), targeting a theoretical molecular weight of 2768 g/mol, Batch E) Prepolymer E made of 46.80 g PEG600, 547.41 g caprolactone and 0.592 g tin(II) octoate (0.03 mole-%), targeting a theoretical molecular weight of 7618 g/mol, Batch F) Prepolymer F made of 330.31 g PEG2000 (5.0 mole-%), 358.09 g caprolactone (94.97 mole-%) and 0.401 g tin(II) octoate (0.03 mole-%), targeting a theoretical molecular weight of 4168 g/mol, Batch G) Prepolymer G made of 152.76 g PEG2000 (1.6 mole-%), 536.06 g caprolactone (98.37 mole-%) and 0.580 g tin(II) octoate (0.03 mole-%), targeting a theoretical molecular weight of 9018 g/mol, Batch H) Prepolymer H made of 549.63 g PEG4000 (10.0 mole-%), 139.38 g caprolactone (89.97 mole-%) and 0.165 g tin(II)octoate (0.03 mole-%), targeting a theoretical molecular weight of 5077 g/mol, Batch I) Prepolymer I made of 447.28 g PEG4000 (5.0 mole-%), 239.45 g caprolactone (94.97 mole-%) and 0.268 g tin(II)

octoate (0.03 mole-%), targeting a theoretical molecular weight of 6218 g/mol, Batch J) Prepolymer J made of 257.29 g PEG4000 (1.6 mole-%), 451.42 g caprolactone (98.37 mole-%) and 0.489 g tin(II) octoate (0.03 mole-%), targeting a theoretical molecular weight of 11018 g/mol, Batch K) Prepolymer K made of 584.57 g PEG8000 (10.0 mole-%), 75.04 g caprolactone (89.97 mole-%) and 0.089 g tin(II) octoate (0.03 mole-%), targeting a theoretical molecular weight of 9027 g/mol and Batch L) Prepolymer L made of 170.77 g PEG8000 (5.0 mole-%), 46.28 g caprolactone (94.97 mole-%) and 0.052 g tin(II) octoate (0.03 mole-%), targeting a theoretical molecular weight of 10168 g/mol.

TABLE 1

Synthesised prepolymers for the present invention.

| Prepolymer Name | PEG | Theoretical MW of prepolymer | Theoretical MW of PCAP block | Number of CL units in PCAP block | Reaction Temperature (° C.), time |
|---|---|---|---|---|---|
| Prepolymer A | 400 | 1013 | 600 | 5 | 160, 5 h |
| Prepolymer B | 400 | 2568 | 1084 | 9.5 | 160, 6 h |
| Prepolymer C | 400 | 7418 | 3509 | 31 | 160, 5 h |
| Prepolymer D | 600 | 2768 | 1084 | 9.5 | 160, 6 h |
| Prepolymer E | 600 | 7618 | 3524 | 31 | 160, 5 h |
| Prepolymer F | 2000 | 4168 | 1100 | 9.5 | 160, 5 h |
| Prepolymer G | 2000 | 9018 | 3500 | 31 | 160, 5 h |
| Prepolymer H | 4000 | 5077 | 538 | 5 | 160, 6 h |
| Prepolymer I | 4000 | 6218 | 1109 | 9.5 | 160, 6 h |
| Prepolymer J | 4000 | 11018 | 3500 | 31 | 160, 5 h |
| Prepolymer K | 8000 | 9027 | 515 | 5 | 160, 5 h |
| Prepolymer L | 8000 | 10168 | 1084 | 9.5 | 160, 5 h |

The molecular weights ($M_n$ and $M_w$) and molecular weight distributions were measured for various prepolymers by a triple angle light scattering combined with size exclusion chromatography (SEC) system. Differential scanning calorimetry (DSC) was used to measure the glass transition temperature, melting point and crystallinity of the prepolymers, see Table 2.

TABLE 2

Prepolymers were characterised using SEC coupled with light scattering and DSC experiments.

| Prepolymer Name | Mn (g/mol) SEC | MWD SEC | $Tg_1$ (° C.) | $Tg_2$ (° C.) | $Tg_3$ (° C.) | $Tm_1$ (° C.) | $Tm_2$ (° C.) | $Tm_3$ (° C.) |
|---|---|---|---|---|---|---|---|---|
| Prepolymer A | — | — | −69.2 | −43.2 | — | −17.0 | 12.4 | 27.2 |
| Prepolymer B | 2249 | 1.37 | −69.3 | −21.6 | 11.0 | 41.6 | 48.3 | — |
| Prepolymer C | 7810 | 1.20 | −67.1 | −19.5 | — | 42.9 | 50.9 | 55.0 |
| Prepolymer D | 2583 | 1.29 | −67.0 | −10.1 | — | 39.8 | 46.7 | 53.1 |
| Prepolymer E | 8623 | 1.35 | −66.9 | −10.4 | — | 46.9 | 53.0 | — |
| Prepolymer F | 4525 | 1.27 | — | — | — | 26.8 | — | — |
| Prepolymer G | 8327 | 1.07 | −65.3 | −3.7 | — | −47.1 | 50.9 | — |
| Prepolymer H | 5584 | 1.02 | −67.1 | −1.2 | — | 50.5 | — | — |
| Prepolymer J | — | — | −66.3 | — | — | 34.7 | 54.6 | — |
| Prepolymer K | — | — | — | — | — | 54.7 | — | — |
| Prepolymer L | — | — | — | — | — | 52.3 | — | — |

EXAMPLE 2

Manufacture of a Linear Bioresorbable Hydrogel Prepolymer and Polymer (Prepolymer M and Polymer 1)

Into a 700 ml stirred tank reactor 319.00 g (10 mole-%) of dried PEG4000 (MW 4050 g/mol), 80.90 g (89.97 mole-%) ε-caprolactone and 0.096 g (0.03 mole-%) tin(II) octoate were fed in that order. Dry nitrogen was continuously purged into the reactor. The reactor was pre-heated to 160° C. using an oil bath and a mixing speed of 100 rpm. PEG4000 was dried and melted in a rota-evaporator prior to being added into the reactor. Then, ε-caprolactone was added and finally the catalyst tin(II) octoate. Prepolymerisation time for the PEG-PCL prepolymer was 4 hours. The theoretical molecular weight of the prepolymer was 5077 g/mol.

For the polymer preparation 400.08 g of low molecular weight poly(ε-caprolactone) diol (MW 530 g/mol) (PCLDI) were fed to the reactor and blended with the above mentioned prepolymer. The mole ratio used for the PEG-PCL prepolymer and polycaprolactone diol was 0.7:1. The blending was done under nitrogen for 30 min using a mixing speed of 100 rpm and a blending temperature of 160° C. The prepolymer and PCLDI mixture was stored in a refrigerator until required.

47.245 g of PEG-PCL prepolymer and PCLDI mixture were fed into a 100 ml reactor and melted at 110° C. for 30 min under nitrogen. Mixing was set at 60 rpm and 3.139 ml of 1,4-butane diisocyanate (BDI), at a molar ratio of 0.7:1.0:1.7 PEG-PCL prepolymer: PCLDI: BDI, were fed into the reactor. Polymerisation time was 17 minutes. Polymer was scraped into an aluminium pan and stored in a desiccator for further testing. (Polymer 1)

EXAMPLE 3

Manufacture of a Linear Bioresorbable Polymer with a Different Structure

Prepolymer H (Table 1 in Example 1), and polycaprolactone diol (MW~530 g/mol) were mixed, dried and melted under vacuum at 70° C. for at least one hour prior to feeding them into the preheated (110° C.) reactor. Reaction mixture was mixed (60 rpm) for 30 min under nitrogen before 1,4-butane diisocyanate was fed into the reactor. The molar ratio between prepolymer, poly(ε-caprolactone) diol and BDI was 0.25:1.0:1.25. The reaction time was 150 minutes. (Polymer 2 and Polymer 3)

DSC analysis revealed that the glass transition temperature ($T_g$) and the melting point ($T_m$) were −48.7 and 38.9° C. respectively. The characteristic peaks of the urethane (N—H, 3341 $cm^{-1}$) and ester bonds (C=O, 1731 $cm^{-1}$) were identified in the bioresorbable polymer using FTIR.

EXAMPLE 4

Manufacture of a Linear Bioresorbable Polymer with a Different Structure

The chain extending polymerisation was performed as in Example 3, except the prepolymer was Prepolymer H in Table 1 in Example 1 and the molar ratio between prepolymer, poly(ε-caprolactone) diol and BDI was 1:1:2. The reaction time was 120 minutes. (Polymer 4).

DSC analysis revealed that the glass transition temperature ($T_g$) and the melting point ($T_m$) were −51.8 and 44.2° C. respectively. The characteristic peaks of the urethane (N—H, 3354 $cm^{-1}$) and ester bonds (C=O, 1728 $cm^{-1}$) were identified in the bioresorbable polymer using FTIR.

EXAMPLE 5

Manufacture of a Linear Bioresorbable Polymer with a Different Structure

The chain extending polymerisation was performed as in Example 3, except the prepolymer was Prepolymer J in Table 1 in Example 1 and the molar ratio between prepolymer, poly(ε-caprolactone) diol and BDI was 1:1:2. The reaction time was 20 minutes. (Polymer 5).

DSC analysis revealed that the glass transition temperature ($T_g$) and the melting points ($T_m$) were −58.9, 17.1 and 44.7° C. respectively. The characteristic peaks of the urethane (N—H, 3384 $cm^{-1}$) and ester bonds (C=O, 1721 $cm^{-1}$) were identified in the bioresorbable polymer using FTIR.

EXAMPLE 6

Manufacture of a Linear Bioresorbable Polymer with a Different Structure

The chain extending polymerisation was performed as in Example 3, except the prepolymer was Prepolymer J in Table 1 in Example 1 and the molar ratio between prepolymer, poly(ε-caprolactone) diol and BDI was 1:1:2.5. The reaction time was 120 minutes. (Polymer 6).

DSC analysis revealed that the glass transition temperature ($T_g$) and the melting points ($T_m$) were −58.7, 16.3 and 43.6° C. respectively. The characteristic peaks of the urethane (N—H, 3381 $cm^{-1}$) and ester bonds (C=O, 1739 $cm^{-1}$) were identified in the bioresorbable polymer using FTIR.

EXAMPLE 7

Manufacture of a Linear Bioresorbable Polymer with a Different Structure

The chain extending polymerisation was performed as in Example 3, except the prepolymer was Prepolymer B in Table 1 in Example 1 and the molar ratio between prepolymer, poly(ε-caprolactone) diol and BDI was 1:1:2.1. The reaction time was 2 minutes. (Polymer 7).

DSC analysis revealed that the glass transition temperature ($T_g$) and the melting point ($T_m$) were −54.1 and 36.1° C. respectively. The characteristic peaks of the urethane (N—H, 3379 $cm^{-1}$) and ester bonds (C=O, 1721 $cm^{-1}$) were identified in the bioresorbable polymer using FTIR.

EXAMPLE 8

Manufacture of a linear bioresorbable polymer with a different structure

The chain extending polymerisation was performed as in Example 3, except the prepolymer was Prepolymer C in Table 1 in Example 1 and the molar ratio between prepolymer, poly(ε-caprolactone) diol and BDI was 1:1:2.1. The reaction time was 60 minutes. (Polymer 8).

DSC analysis revealed that the glass transition temperature ($T_g$) and the melting point ($T_m$) were −61.4 and 49.5° C. respectively. The characteristic peaks of the urethane (N—H, 3387 $cm^{-1}$) and ester bonds (C=O, 1728 $cm^{-1}$) were identified in the bioresorbable polymer using FTIR.

EXAMPLE 9

Manufacture a Linear Bioresorbable Polymer with a Different Structure

The chain extending polymerisation was performed as in Example 3, except the prepolymer was Prepolymer D in Table 1 in Example 1 and the molar ratio between prepolymer, poly(ε-caprolactone) diol and BDI was 1:1:2. The reaction time was 60 minutes. (Polymer 9).

DSC analysis revealed that the glass transition temperature ($T_g$) and the melting point ($T_m$) were −55.7 and 31.7° C. respectively. The characteristic peaks of the urethane (N—H, 3378 $cm^{-1}$) and ester bonds (C=O, 1728 $cm^{-1}$) were identified in the bioresorbable polymer using FTIR.

EXAMPLE 10

Manufacture of a Linear Bioresorbable Polymer with a Different Structure

The chain extending polymerisation was performed as in Example 3, except the prepolymer was Prepolymer D in Table 1 in Example 1 and the molar ratio between prepolymer, poly(ε-caprolactone) diol and BDI was 1:1:2.2. The reaction time was 90 minutes. (Polymer 10).

DSC analysis revealed that the glass transition temperature ($T_g$) and the melting point ($T_m$) were −56.1 and 32.7° C. respectively. The characteristic peaks of the urethane (N—H, 3338 $cm^{-1}$) and ester bonds (C=O, 1721 $cm^{-1}$) were identified in the bioresorbable polymer using FTIR.

EXAMPLE 11

Manufacture of a Linear Bioresorbable Polymer with a Different Structure

The chain extending polymerisation was performed as in Example 3, except the prepolymer was Prepolymer E in Table 1 in Example 1 and the molar ratio between prepolymer, poly(ε-caprolactone) diol and BDI was 1:1:2. The reaction time was 60 minutes. (Polymer 11).

DSC analysis revealed that the glass transition temperature ($T_g$) and the melting point ($T_m$) were −61.1 and 49.1° C. respectively. The characteristic peaks of the urethane (N—H, 3386 cm$^{-1}$) and ester bonds (C=O, 1728 cm$^{-1}$) were identified in the bioresorbable polymer using FTIR.

EXAMPLE 12

Manufacture of a Linear Bioresorbable Polymer with a Different Structure

The chain extending polymerisation was performed as in Example 3, except the prepolymer was Prepolymer F in Table 1 in Example 1 and the molar ratio between prepolymer, poly(ε-caprolactone) diol and BDI was 1:1:2.2. The reaction time was 120 minutes. (Polymer 12).

DSC analysis revealed that the glass transition temperature ($T_g$) and the melting point ($T_m$) were −55.4 and 22.2° C. respectively. The characteristic peaks of the urethane (N—H, 3381 cm$^{-1}$) and ester bonds (C=O, 1732 cm$^{-1}$) were identified in the bioresorbable polymer using FTIR.

EXAMPLE 13

Manufacture of a Linear Bioresorbable Polymer with a Different Structure

The chain extending polymerisation was performed as in Example 3, except the prepolymer was Prepolymer G in Table 1 in Example 1 and the molar ratio between prepolymer, poly(ε-caprolactone) diol and BDI was 1:1:2. The reaction time was 120 minutes. (Polymer 13).

DSC analysis revealed that the glass transition temperature ($T_g$) and the melting point ($T_m$) were −63.4 and 44.1° C. respectively. The characteristic peaks of the urethane (N—H, 3384 cm$^{-1}$) and ester bonds (C=O, 1721 cm$^{-1}$) were identified in the bioresorbable polymer using FTIR.

EXAMPLE 14

Manufacture of a Linear Bioresorbable Polymer with a Different Structure

The chain extending polymerisation was performed as in Example 3, except the prepolymer was Prepolymer K in Table 1 in Example 1 and the molar ratio between prepolymer, poly(ε-caprolactone) diol and BDI was 1:1:2. The reaction time was 120 minutes. (Polymer 14).

DSC analysis revealed that the glass transition temperature ($T_g$) and the melting point ($T_m$) were −51.5 and 52.1° C. respectively. The characteristic peaks of the urethane (N—H, 3357 cm$^{-1}$) and ester bonds (C=O, 1732 cm$^{-1}$) were identified in the bioresorbable polymer using FTIR.

TABLE 3

Synthesised bioresorbable polymers for the present invention.

| Polymer Name | PEG | Prepolymer Name | Theoretical MW of prepolymer | Theoretical MW of CAP block | Prepolymer Mol ratio | CAP-diol Mol ratio | BDI | Reaction Temperature (° C.), time |
|---|---|---|---|---|---|---|---|---|
| Polymer 8 | 400 | Prepolymer C | 7418 | 3509 | 1 | 1 | 2.1 | 120, 1 h |
| Polymer 7 | 400 | Prepolymer B | 2568 | 1084 | 1 | 1 | 2.1 | 120, 2 min |
| Polymer 11 | 600 | Prepolymer E | 7618 | 3524 | 1 | 1 | 2 | 120, 1 h |
| Polymer 9 | 600 | Prepolymer D | 2768 | 1084 | 1 | 1 | 2 | 120, 1 h |
| Polymer 15 | 600 | Prepolymer D | 2768 | 1084 | 1 | 1 | 2.1 | 120, 1 h |
| Polymer 10 | 600 | Prepolymer D | 2768 | 1084 | 1 | 1 | 2.2 | 120, 1 h 30 min |
| Polymer 16 | 2000 | Prepolymer F | 4168 | 1100 | 1 | 1 | 2 | 110, 2 h |
| Polymer 17 | 2000 | Prepolymer F | 4168 | 1100 | 1 | 1 | 2.1 | 110, 2 h |
| Polymer 12 | 2000 | Prepolymer F | 4168 | 1100 | 1 | 1 | 2.2 | 110, 2 h |
| Polymer 13 | 2000 | Prepolymer G | 9018 | 3500 | 1 | 1 | 2 | 110, 2 h |
| Polymer 18 | 2000 | Prepolymer G | 9018 | 3500 | 1 | 1 | 2.1 | 110, 2 h |
| Polymer 19 | 2000 | Prepolymer G | 9018 | 3500 | 1 | 1 | 2.2 | 110, 2 h |
| Polymer 20 | 2000 | Prepolymer G | 9018 | 3500 | 1 | 1 | 2.2 | 140, 2 h |
| Polymer 1 | 4000 | Prepolymer M | 5077 | 538 | 0.7 | 1 | 1.7 | |
| Polymer 21 | 4000 | Prepolymer M | 5077 | 538 | 0.7 | 1 | 1.53 | |
| Polymer 22 | 4000 | Prepolymer M | 5077 | 538 | 0.7 | 1 | 1.36 | |
| Polymer 23 | 4000 | One-pot | 5077 | 538 | 0.7 | 1 | 1.53 | 160, 6 min |
| Polymer 2 | 4000 | Prepolymer H | 5077 | 538 | 0.25 | 1 | 1.25 | 110, 2 h 30 min |
| Polymer 24 | 4000 | Prepolymer H | 5077 | 538 | 0.25 | 1 | 1.4 | 110, 2 h |
| Polymer 3 | 4000 | Prepolymer H | 5077 | 538 | 0.25 | 1 | 1.25 | 110, 2 h 25 min |
| Polymer 4 | 4000 | Prepolymer H | 5077 | 538 | 1 | 1 | 2 | 110, 2 h |
| Polymer 25 | 4000 | Prepolymer I | 6218 | 1109 | 0.25 | 1 | 1.25 | 110, 4 h |
| Polymer 26 | 4000 | Prepolymer I | 6218 | 1109 | 0.25 | 1 | 1.25 | 110, 2 h |
| Polymer 27 | 4000 | Prepolymer I | 6218 | 1109 | 0.25 | 1 | 1.25 | 110, 2 h |
| Polymer 5 | 4000 | Prepolymer J | 11018 | 3500 | 1 | 1 | 2 | 110, 20 min |
| Polymer 28 | 4000 | Prepolymer J | 11018 | 3500 | 1 | 1 | 2.1 | 110, 30 min |
| Polymer 30 | 4000 | Prepolymer J | 11018 | 3500 | 1 | 1 | 2.2 | 110, 20 min |
| Polymer 31 | 4000 | Prepolymer J | 11018 | 3500 | 1 | 1 | 2.2 | 140, 1 h |
| Polymer 32 | 4000 | Prepolymer J | 11018 | 3500 | 1 | 1 | 2.3 | 110, 1 h |
| Polymer 33 | 4000 | Prepolymer J | 11018 | 3500 | 1 | 1 | 2.4 | 110, 2 h |
| Polymer 6 | 4000 | Prepolymer J | 11018 | 3500 | 1 | 1 | 2.5 | 110, 2 h |
| Polymer 14 | 8000 | Prepolymer K | 9027 | 515 | 1 | 1 | 2 | 110, 2 h |
| Polymer 34 | 8000 | Prepolymer K | 9027 | 515 | 1 | 1 | 2.1 | 110, 2 h |
| Polymer 35 | 8000 | Prepolymer K | 9027 | 515 | 1 | 1 | 2.2 | 110, 2 h |

EXAMPLE 15

Molecular weight determination was carried out for a selected number of bioresorbable polymers, which are shown in Table 4. The molecular weight of the polymer will determine its mechanical properties and have an impact on its degradation properties; therefore the importance of determining molecular weight values is evident.

These types of polymers are expected to have a molecular weight of 100,000 ($M_n$) in the best of cases. The minimum value for the $M_n$ to have reasonable mechanical properties or to consider the compound a polymer is 30,000. In the present invention molecular weight values for $M_n$ exceeded our expectations and values of well over 100,000 were obtained in most cases.

TABLE 4

Molecular weight analyses for selected bioresorbable polymers.

| Example Number | Polymer Name | Prepolymer PEG | Prepolymer Name | Mw (g/mol) SEC | Mn (g/mol) SEC | MWD SEC |
|---|---|---|---|---|---|---|
|  | Polymer 16 | 2000 | Prepolymer F | 71,030 | 25,380 | 2.80 |
| 12 | Polymer 12 | 2000 | Prepolymer F | 343,600 | 251,600 | 1.37 |
|  | Polymer 18 | 2000 | Prepolymer G | 238,300 | 141,900 | 1.68 |
|  | Polymer 19 | 2000 | Prepolymer G | 218,400 | 126,600 | 1.72 |
|  | Polymer 20 | 2000 | Prepolymer G | 209,700 | 129,000 | 1.62 |
| 4 | Polymer 4 | 4000 | Prepolymer H | 206,700 | 131,700 | 1.57 |
| 5 | Polymer 5 | 4000 | Prepolymer J | 145,100 | 84,750 | 1.71 |
|  | Polymer 28 | 4000 | Prepolymer J | 191,400 | 126,700 | 1.51 |
|  | Polymer 30 | 4000 | Prepolymer J | 163,300 | 102,400 | 1.59 |
|  | Polymer 31 | 4000 | Prepolymer J | 146,900 | 87,210 | 1.68 |
|  | Polymer 32 | 4000 | Prepolymer J | 185,500 | 111,100 | 1.67 |
|  | Polymer 33 | 4000 | Prepolymer J | 136,600 | 76,960 | 1.77 |
| 6 | Polymer 6 | 4000 | Prepolymer J | 130,700 | 73,610 | 1.78 |
| 14 | Polymer 14 | 8000 | Prepolymer K | 198,300 | 153,900 | 1.29 |
|  | Polymer 34 | 8000 | Prepolymer K | 170,200 | 116,900 | 1.46 |
|  | Polymer 35 | 8000 | Prepolymer K | 160,600 | 115,700 | 1.39 |

EXAMPLE 16

Purification of Bioresorbable Polymers by Solvent Precipitation

The polymers from Example 2 and 3 were purified after polymerisation by precipitation into a non-solvent. Initially the polymers were dissolved using dichloro methane (DCM), chloroform or tetrahydrofuran (THF) as solvents and diethyl ether as the precipitating solvent. Precipitated polymers were vacuum dried and kept in a desiccator until further testing was required.

EXAMPLE 17

Processing of Thermoplastic Polymers by Using a Hot-Press and Solvent Casting—Film Production The bioresorbable polymers from Example 3 were dried under vacuum over night prior to processing them using the hot-press. Upper and lower plate temperatures were set at 130° C. Two Teflon sheets were placed between the mould and the hot plates. The melting time was 2 min followed by a 30 second holding under pressure (~170 bar). An exact amount of polymer was used to fill the mould. After cooling to room temperature samples (30 mm×10 mm×1 mm) were mechanically punched out and kept in the freezer for further analysis.

Solvent cast films: a number of polymers from Table 3 were dissolved in DCM and poured into aluminium pans followed by overnight solvent evaporation in the fume cupboard.

EXAMPLE 18

One Month Degradation Investigation at 37° C. in Water

In order to prove the bioresorbability of the synthesised polymers, a few polymers were selected to carry out biodegradation studies (Examples 18-20).

Figure 1:
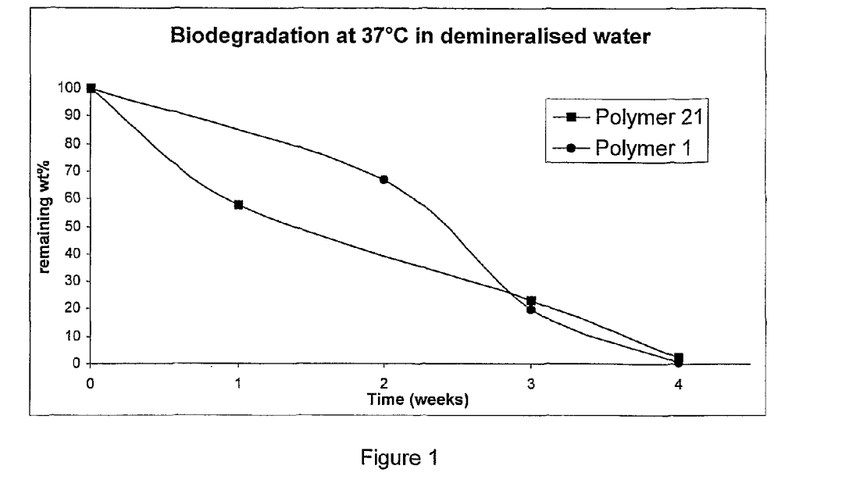
FIG. 1 shows the biodegradation of Polymer 21 and Polymer 1 in demineralised water at 37° C.
Figure 2:
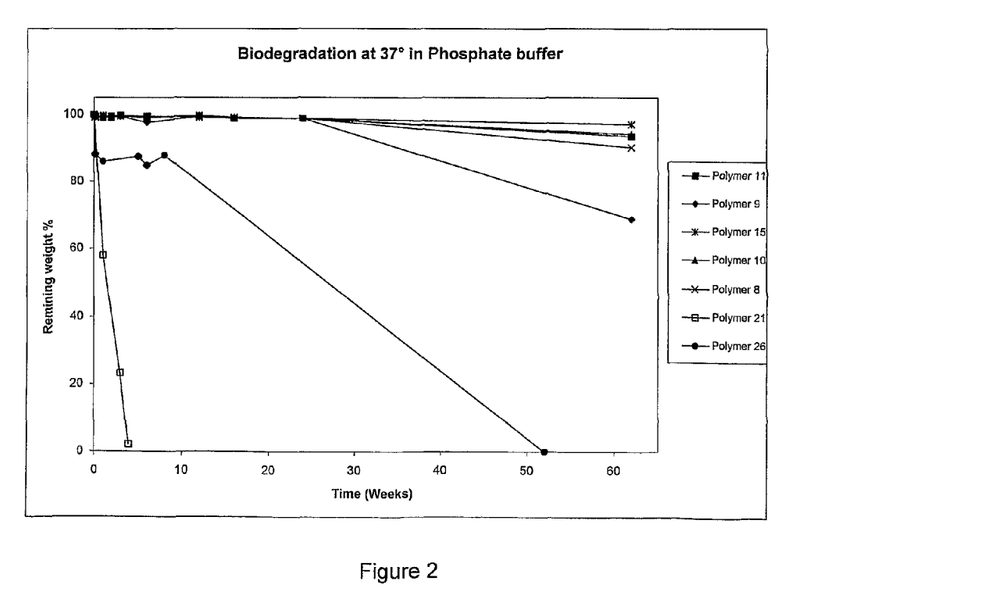
FIG. 2 shows the biodegradation of Polymer 11, Polymer 9, Polymer 15, Polymer 10, Polymer 8, Polymer 21 and Polymer 26 in phosphate buffer at 37° C.
Figure 3:
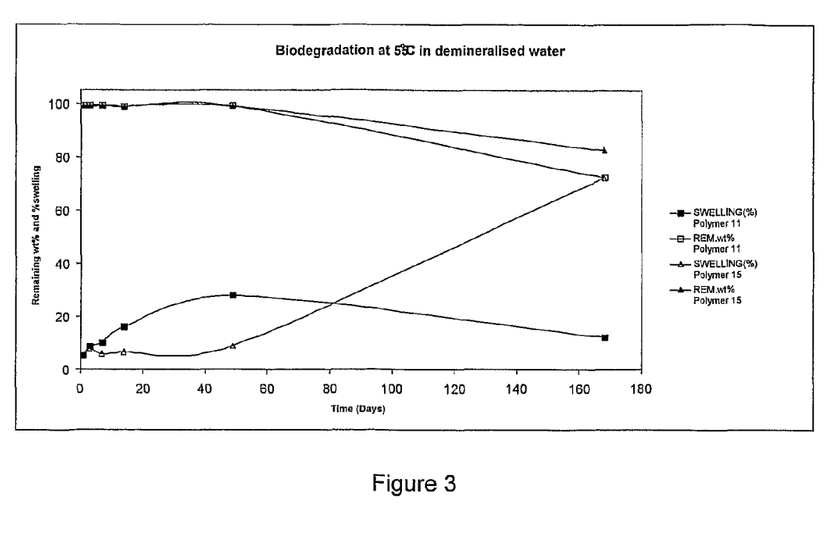
FIG. 3 shows the biodegradation of Polymer 11 and Polymer 15 in demineralised water at 55° C.

Polymer samples (size 30×10×1 mm) for degradation studies were made from the biodegradable polymers by hot-pressing films and punching specimens out of it. There were 2 different types of degradation studies: one at 37° C. in phosphate buffer saline solution pH 7.4 (for 6-16 months) Example 19 and another one in water (for 1 month) Example 18 and an accelerated study at 55° C. in demineralised water (for 3 months) Example 20. At the beginning samples were taken every week and after one month once a month or even less frequently. The degradation results at 37° C. in water and in phosphate buffer can be seen in FIGS. 1 and 2, respectively. The accelerated degradation can be found in FIG. 3.

Without wishing to be bound by theory, it is believed that the degradation mechanism of bulk degrading/eroding polymers, which is typical for most polyester based polymers, consists of two main stages. In the first stage, the molecular weight of the polymer starts to degrade and the water uptake or swelling % increases. At a later stage, when the molecular weight of the polymer decreases below 15000 g/mol the weight or mass loss starts to occur. *Biomaterials*, 1981, 2, 215-220. The limit for the weight loss to happen depends on the nature of the polymer and its solubility in the surrounding media. Hydrophilic and hydrophobic blocks may change the degradation mechanism. For example extremely hydrophobic polymers with hydrolytically labile bonds produce surface eroding polymers while hydrophilic structure units in the polyesters may remove the autocatalytic effect of acidic degradation products and produce "real" bulk degradation without the empty shell effect.

EXAMPLE 19

Fifteen Months Degradation Investigation at 37° C. in Buffered Saline Solution

The pessaries for the biodegradation study were prepared as in Example 18. The degradation could be readily tailored by changing the polymer. Polymers were tailor made to suit degradation.

EXAMPLE 20

Six Months Degradation Investigation at 55° C. in Demineralised Water

The pessaries for the biodegradation study were prepared as in Example 18. The higher temperature increased the degradation rate.

The Applicant of the present invention has therefore, in at least one embodiment, provided a bioresorbable polymer obtainable from caprolactone and PEG, which differs from previous polymers in composition, properties, manufacturing method, degradation rate and use.

The applicant of the present invention has found that the properties of previous bioresorbable polymers were dependent on either the caprolactone or PEG properties. By using diisocyanate, which extends the polymer chains and a caprolactone diol, the polymers of the present invention can incorporate aspects of all moieties. Surprisingly, the applicant has found that the combination of three polymerisation techniques gives a greater control over the polymer structure, resulting in extremely useful properties.

The above described specific embodiments are not to be considered to limit the invention described herein.

The invention claimed is:

1. A polymer obtained by reacting together:
   (a) a prepolymer comprising co-polymerised units of a caprolactone and poly(alkylene oxide) moieties;
   (b) a polycaprolactone diol comprising co-polymerised units of a caprolactone and a $C_2$-$C_6$ diol, the $C_2$-$C_6$ diol having a lower molecular weight than the poly(alkylene oxide) of prepolymer (a); and
   (c) a diisocyanate;
   wherein the molar ratio of component (a) to component (b) to component (c) is in the range of about 0.15-1.5 to about 1.0 to about 1.0-2.75 and the polymer is a linear polymer.

2. The polymer according to claim 1, wherein the poly(alkylene oxide) of prepolymer (a) is a poly ($C_2$-$C_3$ alkylene oxide) or mixture thereof.

3. The polymer according to claim 1, wherein the poly(alkylene oxide) is poly(ethylene glycol).

4. The polymer according to claim 3, wherein the poly(ethylene glycol) has the structure $HO(CH_2CH_2O)_nH$ wherein n is an integer from 1 to 800.

5. The polymer according to claim 3, wherein the poly(ethylene glycol) has an average molecular weight of 300 g/mol to 10,000 g/mol.

6. The polymer according to claim 5 wherein the poly(ethylene glycol) has an average molecular weight of 400 g/mol to 10,000 g/mol.

7. The polymer according to claim 1, wherein prepolymer (a) is a block copolymer of structure $(CAP)_n$-PEG-$(CAP)_n$, where CAP is caprolactone and PEG is polyethylene glycol; and n in each CAP block is from 3 to 40.

8. The polymer according to claim 7 wherein n is from 5 to 31.

9. The polymer according to claim 3 wherein molar ratio of caprolactone to poly(ethylene glycol) in prepolymer (a) is from 2:1 up to 124:1.

10. The polymer according to claim 1, wherein the polymer is obtained by reacting components (a), (b), and (c) together with a polymerisation catalyst, wherein the polymerisation catalyst is stannous octoate.

11. The polymer according to claim 1 wherein the $C_2$-$C_6$ diol of component (b) has the structure $HO-(CH_2)_m-OH$ wherein m is from 2 to 6.

12. The polymer according to claim 1 wherein the $C_2$-$C_6$ diol of component (b) is a poly(ethylene oxide).

13. The A polymer according to claim 1 wherein the $C_2$-$C_6$ diol of component (b) is ethylene glycol and the molar ratio of caprolactone to ethylene glycol in component (b) is 4 or 2.

14. The A polymer according to claim 1 wherein the diisocyanate (c) is 1,6-hexamethylene diisocyanate or L-lysine diisocyanate.

15. The polymer according to claim 1 wherein the diisocyanate (c) is 1,4-butane diisocyanate.

16. A delivery device, which comprises the polymer of claim 1 loaded with an active agent.

17. The drug delivery device according to claim 16, wherein the active agent is a pharmaceutically active agent.

18. A method for preparing the polymer of claim 1, which comprises reacting together components (a), (b) and (c).

19. A pharmaceutical composition, comprising the polymer of claim 1 and a releasable pharmaceutically active agent.

20. The composition of claim 19, where in the composition is in a solid dosage form.

21. The polymer of claim 1, wherein the molar ratio of component (a) to component (b) to component (c) is in the range of about 0.2-1.0 to about 1.0 to about 1.25-2.5.

22. The polymer of claim 1, wherein the molar ratio of component (a) to component (b) to component (c) is in the range of about 0.25-1.0 to about 1.0 to about 2.5.

23. The delivery device of claim 16, wherein the poly(alkylene oxide) of prepolymer (a) is a poly ($C_2$-$C_3$ alkylene oxide) or mixture thereof.

24. The delivery device of claim 23, wherein the poly(alkylene oxide) is poly(ethylene glycol).

25. The delivery device of claim 24, wherein the poly(ethylene glycol) has the structure $HO(CH_2CH_2O)_nH$, in which is an integer from 1 to 800.

26. The delivery device of claim 24, wherein the poly(ethylene glycol) has an average molecular weight of 300 g/mol to 10,000 g/mol.

27. The delivery device of claim 26, wherein the poly(ethylene glycol) has an average molecular weight of 400 g/mol to 10,000 g/mol.

28. The delivery device of claim 16, wherein prepolymer (a) is a block copolymer of structure $(CAP)_n$-PEG-$(CAP)_n$, where CAP is caprolactone and PEG is polyethylene glycol; and n in each CAP block is from 3 to 40.

29. The delivery device of claim 28, wherein n is from 5 to 31.

30. The delivery device of claim 24, wherein molar ratio of caprolactone to poly(ethylene glycol) in prepolymer (a) is from 2:1 up to 124:1.

31. The delivery device of claim 16, wherein the polymer is obtained by reacting components (a), (b), and (c) together with a polymerisation catalyst, wherein the polymerisation catalyst is stannous octoate.

32. The delivery device of claim 16, wherein the $C_2$-$C_6$ diol of component (b) has the structure $HO-(CH_2)_m-OH$, in which m is from 2 to 6.

33. The delivery device of claim 16, wherein the $C_2$-$C_6$ diol of component (b) is a poly(ethylene oxide).

34. The delivery device of claim 16, wherein the $C_2$-$C_6$ diol of component (b) is ethylene glycol and the molar ratio of caprolactone to ethylene glycol in component (b) is 4 or 2.

35. The delivery device of claim 16, wherein the diisocyanate (c) is 1,6-hexamethylene diisocyanate or L-lysine diisocyanate.

36. The delivery device of claim 16, wherein the diisocyanate (c) is 1,4-butane diisocyanate.

37. The delivery device of claim 16, wherein the molar ratio of component (a) to component (b) to component (c) is in the range of about 0.2-1.0 to about 1.0 to about 1.25-2.5.

38. The delivery device of claim 16, wherein the molar ratio of component (a) to component (b) to component (c) is in the range of about 0.25-1.0 to about 1.0 to about 2.5.

* * * * *

UNITED STATES PATENT AND TRADEMARK OFFICE
CERTIFICATE OF CORRECTION

PATENT NO. : 8,524,254 B2  
APPLICATION NO. : 12/446235  
DATED : September 3, 2013  
INVENTOR(S) : Donald Magnus Nicolson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 901 days.

Signed and Sealed this
Seventeenth Day of February, 2015

Michelle K. Lee
*Deputy Director of the United States Patent and Trademark Office*